United States Patent
Sullivan

(10) Patent No.: US 7,574,902 B2
(45) Date of Patent: Aug. 18, 2009

(54) TEAR FILM OSMOMETRY

(75) Inventor: Benjamin D. Sullivan, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 283 days.

(21) Appl. No.: 11/358,986

(22) Filed: Feb. 21, 2006

(65) Prior Publication Data

US 2006/0137435 A1 Jun. 29, 2006

Related U.S. Application Data

(63) Continuation of application No. 10/400,617, filed on Mar. 25, 2003, now Pat. No. 7,017,394.

(60) Provisional application No. 60/401,432, filed on Aug. 6, 2002.

(51) Int. Cl.
*G01N 13/04* (2006.01)

(52) U.S. Cl. .................. 73/64.47; 73/64.56; 73/864.01; 324/692

(58) Field of Classification Search ............... 73/64.47, 73/64.56, 864.01; 324/692; 364/692
See application file for complete search history.

(56) References Cited

U.S. PATENT DOCUMENTS 4,028,931 A 6/1977 Bisera et al.

(Continued)

FOREIGN PATENT DOCUMENTS

DE 3414866 A1 10/1985

(Continued)

OTHER PUBLICATIONS

BIOSIS abstract #002246922, Claudino et al., "The role of cGMP on uroguanylin responses in salt-loaded rats," Annual Meeting of Professional Research Scientists on Experimental Biology, New Orleans, Louisiana, USA, Apr. 20-24, 2002; FASEB Journal 16:A956, Mar. 22, 2002.

(Continued)

*Primary Examiner*—Hezron Williams
*Assistant Examiner*—Gunnar J Gissel
(74) *Attorney, Agent, or Firm*—Townsend and Townsend and Crew LLP

(57) ABSTRACT

Osmolarity measurement of a sample fluid, such as tear film, is achieved by depositing an aliquot-sized sample on a sample receiving substrate. The sample fluid is placed on a sample region of the substrate. Energy is imparted to the sample fluid and energy properties of the fluid can be detected to produce a sample fluid reading that indicates osmolarity of the sample fluid. An aliquot-sized volume can comprise, for example, a volume of no more than 20 microliters (μL). The aliquot-sized sample volume can be quickly and easily obtained, even from dry eye sufferers. The imparted energy can comprise electrical, optical or thermal energy. In the case of electrical energy, the energy property of the sample fluid can comprise electrical conductivity. In the case of optical energy, the energy property can comprise fluorescence. In the case of thermal energy, the measured property can be the freezing point of the sample fluid. The substrate can be packaged into a chip, such as by using semiconductor fabrication techniques. An ex vivo osmolarity sensor system that uses the chip can detect energy from the sample region and can provide an accurate osmolarity measurement without user intervention.

39 Claims, 11 Drawing Sheets

U.S. PATENT DOCUMENTS

| | | | |
|---|---|---|---|
| 4,123,701 A * | 10/1978 | Josefsen et al. | ............. 324/448 |
| 4,150,564 A | 4/1979 | Barlow et al. | |
| 4,245,495 A | 1/1981 | Kakiuchi et al. | |
| 4,269,197 A | 5/1981 | Gilbard | |
| 4,305,823 A | 12/1981 | Batzer et al. | |
| 4,455,864 A | 6/1984 | Wallner | |
| 4,475,556 A | 10/1984 | Reiff | |
| 4,603,699 A | 8/1986 | Himpens | |
| 4,706,495 A | 11/1987 | Steudle et al. | |
| 4,951,683 A * | 8/1990 | Davis | .......................... 600/383 |
| 4,996,993 A | 3/1991 | York | |
| 5,005,403 A | 4/1991 | Steudle et al. | |
| 5,143,080 A * | 9/1992 | York | .......................... 600/549 |
| 5,211,055 A | 5/1993 | Steudle et al. | |
| 5,230,864 A | 7/1993 | Columbus | |
| 5,388,449 A | 2/1995 | LeVeen et al. | |
| 5,591,636 A | 1/1997 | Grass | |
| 5,665,904 A | 9/1997 | Boling | |
| 5,766,435 A | 6/1998 | Liao et al. | |
| 5,869,231 A | 2/1999 | Romisch et al. | |
| 6,224,550 B1 | 5/2001 | Ellingsen | |
| 6,894,511 B2 * | 5/2005 | Yukimasa et al. | ........... 324/692 |
| 2002/0031813 A1 | 3/2002 | Ozkan et al. | |
| 2002/0094580 A1 * | 7/2002 | Jorgenson et al. | ........... 436/151 |
| 2002/0182627 A1 | 12/2002 | Wang et al. | |

FOREIGN PATENT DOCUMENTS

| | | | |
|---|---|---|---|
| EP | 0571066 A2 | 11/1993 | |
| WO | WO 96/14571 | 5/1996 | |
| WO | WO 99/23938 | 5/1999 | |
| WO | WO 02/103354 | 12/2002 | |

OTHER PUBLICATIONS

Certified English Translation for German Patent No. DE 3414866 (item E) entitled: "Method and device to measure the osmolarity of liquid samples," Oct. 31, 1985.

Ogasawara et al., "Electrical conductivity of tear fluid in healthy persons and keratoconjunctivitis sicca patients measured by a flexible conductimetric sensor," Graefe's Arch Clin Exp Opthalmol. 234:542-546 (1996).

M. Lemp, "Report of the National Eye Institute/Industry Workshop on Clinical Trials in Dry Eyes", The CLAO Journal, vol. 21, No. 4, Oct. 1995, pp. 221-232.

J.P. Bilbard et al., "Changes in Tear Ion Concentrations in Dry-Eye Disorders", May 2001, pp. 529-533.

C.D. Pensyl et al., "Vapor Pressure Osmometry: Minimum Sample Microvolumes", ACTA Ophtalmol Scan 77 (1), Feb. 1999, pp. 27-30.

A.J. Grodzinsky, "Fields, Forces and Flows in Biological Tissues and Membranes", MIT Department of Electrical Engineering, 1995, pp. 191-197.

R.L. Farris, "Tear Osmolarity—A New Gold Standard", 1994, pp. 495-503.

D.A. Schaumberg, "Aging and Sex-Steroid Hormone Influences in Dry Eye Syndrome", ARVO abstract from IOVS, Mar. 15, 2001, vol. 42, No. 4.

* cited by examiner

TEAR FILM OSMOMETRY

REFERENCE TO PRIORITY DOCUMENT

This continuation application claims the benefit of priority of U.S. application Ser. No. 10/400,617 filed Mar. 25, 2003 now U.S. Pat. No. 7,017,394 by Benjamin D. Sullivan, entitled "Tear Film Osmometry", now U.S. Pat. No. 7,017,394 issued Mar. 28, 2006, which claims priority to U.S. Provisional Patent Application Ser. No. 60/401,432 entitled "Volume Independent Tear Film Osmometer", by Benjamin D. Sullivan, filed Aug. 6, 2002. Priority of the filing date of these applications is hereby claimed, and the disclosures of the applications are hereby incorporated by reference.

BACKGROUND

1. Field

The present invention relates generally to measuring the osmotic pressure of fluids and, more particularly, to measuring the osmolarity of tear film.

2. Description of the Related Art

Tears fulfill an essential role in maintaining ocular surface integrity, protecting against microbial challenge, and preserving visual acuity. These functions, in turn, are critically dependent upon the composition and stability of the tear film structure, which includes an underlying mucin foundation, a middle aqueous component, and an overlying lipid layer. Disruption, deficiency, or absence of the tear film can severely impact the eye. If unmanaged with artificial tear substitutes or tear film conservation therapy, these disorders can lead to intractable desiccation of the corneal epithelium, ulceration and perforation of the cornea, an increased incidence of infectious disease, and ultimately pronounced visual impairment and blindness.

Keratoconjunctivitis sicca (KCS), or "dry eye", is a condition in which one or more of the tear film structure components listed above is present in insufficient volume or is otherwise out of balance with the other components. It is known that the fluid tonicity or osmolarity of tears increases in patients with KCS. KCS is associated with conditions that affect the general health of the body, such as Sjogren's syndrome, aging, and androgen deficiency. Therefore, osmolarity of a tear film can be a sensitive and specific indicator for the diagnosis of KCS and other conditions.

The osmolarity of a sample fluid (e.g., a tear) can be determined by an ex vivo technique called "freezing point depression," in which solutes or ions in a solvent (i.e. water), cause a lowering of the fluid freezing point from what it would be without the ions. In the freezing point depression analysis, the freezing point of the ionized sample fluid is found by detecting the temperature at which a quantity of the sample (typically on the order of about several milliliters) first begins to freeze in a container (e.g., a tube). To measure the freezing point, a volume of the sample fluid is collected into a container, such as a tube. Next, a temperature probe is immersed in the sample fluid, and the container is brought into contact with a freezing bath or Peltier cooling device. The sample is continuously stirred so as to achieve a supercooled liquid state below its freezing point. Upon mechanical induction, the sample solidifies, rising to its freezing point due to the thermodynamic heat of fusion. The deviation from the sample freezing point from 0° C. is proportional to the solute level in the sample fluid. This type of measuring device is sometimes referred to as an osmometer.

Presently, freezing point depression measurements are made ex vivo by removing tear samples from the eye using a micropipette or capillary tube and measuring the depression of the freezing point that results from heightened osmolarity. However, these ex vivo measurements are often plagued by many difficulties. For example, to perform freezing point depression analysis of the tear sample, a relatively large volume must be collected, typically on the order of 20 microliters (μL) of a tear film. Because no more than about 10 to 100 nanoliters (nL) of tear sample can be obtained at any one time from a KCS patient, the collection of sufficient amounts of fluid for conventional ex vivo techniques requires a physician to induce reflex tearing in the patient. Reflex tearing is caused by a sharp or prolonged irritation to the ocular surface, akin to when a large piece of dirt becomes lodged in one's eye. Reflex tears are more dilute, i.e. have fewer solute ions than the tears that are normally found on the eye. Any dilution of the tear film invalidates the diagnostic ability of an osmolarity test for dry eye, and therefore make currently available ex vivo methods prohibitive in a clinical setting.

A similar ex vivo technique is vapor pressure osmometry, where a small, circular piece of filter paper is lodged underneath a patient's eyelid until sufficient fluid is absorbed. The filter paper disc is placed into a sealed chamber, whereupon a cooled temperature sensor measures the condensation of vapor on its surface. Eventually the temperature sensor is raised to the dew point of the sample. The reduction in dew point proportional to water is then converted into osmolarity. Because of the induction of reflex tearing and the large volume requirements for existing vapor pressure osmometers, they are currently impractical for determination of dry eye.

The Clifton Nanoliter Osmometer (available from Clifton Technical Physics of Hartford, N.Y., USA) has been used extensively in laboratory settings to quantify the solute concentrations of KCS patients, but the machine requires a significant amount of training to operate. It generally requires hour-long calibrations and a skilled technician in order to generate acceptable data. The Clifton Nanoliter Osmometer is also bulky and relatively expensive. These characteristics seriously detract from its use as a clinical osmometer.

In contrast to ex vivo techniques that measure osmolarity of tear samples removed from the ocular surface, an in vivo technique that attempted to measure osmolarity directly on the ocular surface used a pair flexible pair of electrodes that were placed directly underneath the eyelid of the patient. The electrodes were then plugged into an LCR meter to determine the conductivity of the fluid surrounding them. While it has long been known that conductivity is directly related to the ionic concentration, and hence osmolarity of solutions, placing the sensor under the eyelid for half a minute likely induced reflex tearing. Furthermore, these electrodes were difficult to manufacture and posed increased health risks to the patient as compared to simply collecting tears with a capillary.

It should be apparent from the discussion above that current osmolarity measurement techniques are unavailable in a clinical setting and can't attain the volumes necessary for dry eye patients. Thus, there is a need for an improved, clinically feasible, nanoliter-scale osmolarity measurement. The present invention satisfies this need.

SUMMARY

Osmolarity measurement of a sample fluid, such as a tear film, is achieved by depositing an aliquot volume of the sample fluid on a microchip having a substrate and a sample region of the substrate, wherein the volume of the sample fluid operatively covers a sufficient portion of the sample region such that energy imparted to the sample fluid is detected from the sample region to produce an output signal that indicates osmolarity of the sample fluid. Thus, an osmolarity measurement of the sample fluid can be obtained from the detected energy of the sample volume. The aliquot-sized sample volume can be quickly and easily obtained, even from dry eye patients. An aliquot volume can comprise, for example, a volume of no more than 20 microliters (μL), but can be as little as 1 nL. An osmolarity sensor system can receive the microchip and sample volume, and can detect energy from the sample volume to display an accurate osmolarity measurement. In this way, a reliable osmolarity measurement can be obtained with minimum inconvenience and discomfort to a patient, without requiring a great deal of skill to obtain the measurement, and with a high degree of repeatability and accuracy.

The sample fluid volume can be easily deposited on the substrate sample region. Energy is transferred to the sample fluid such that energy properties of the sample fluid can be detected to provide an accurate measurement of sample osmolarity. The energy transferred can comprise electrical energy. For example, electrodes of the substrate can be spaced such that an aliquot-sized sample volume can bridge at least two of the electrodes. Electrical energy passing through the electrodes can be used to measure conductivity and thereby provide an osmolarity measure. The energy transferred can comprise optical energy. For example, nanometer-sized spheres can be coated with luminescent ion-sensitive chemicals. When the spheres are exposed to a tear film sample and are excited with light energy such as laser light, the spheres will luminesce such that the emitted light can be correlated to osmolarity of the sample. The energy transferred can comprise thermal energy. Continuous cooling of the sample results in a reduced conductivity of the sample upon freezing, which allows correlation of the determined freezing point with the osmolarity of the sample.

An osmolarity sensor system for measuring osmolarity of a sample fluid includes a sample fluid reception device and a platform for data communication. The sample fluid reception device can be produced, for example, using semiconductor fabrication techniques. Microprocessor fabrication techniques allow the reception device to be as simple as a set of electrodes printed on a microchip, or as complicated as a logic-enabled microprocessor capable of enacting measurement dynamics on the sample fluid reception element. Microfabrication also enables temperature sensing and temperature control directly on the sample fluid reception device. The platform for data communication receives output from the sample fluid reception device, and interprets and displays this information as an osmolarity of the sample fluid to the user via LCD or equivalent display mechanism.

Other features and advantages of the present invention should be apparent from the following description of the preferred embodiment, which illustrates, by way of example, the principles of the invention.

DETAILED DESCRIPTION

Exemplary embodiments are described for measuring the osmolarity of an aliquot volume of a sample fluid (e.g., tear film, sweat, blood, or other fluids). The exemplary embodiments are configured to be relatively fast, non-invasive, inexpensive, and easy to use, with minimal injury of risk to the patient. Accurate measurements can be provided with as little as nanoliter volumes of a sample fluid. For example, a measuring device configured in accordance with the invention enables osmolarity measurement with no more than 20 μL of sample fluid, and typically much smaller volumes can be successfully measured. In one embodiment described further below, osmolarity measurement accuracy is not compromised by variations in the volume of sample fluid collected, so that osmolarity measurement is substantially independent of collected volume. The sample fluid can include tear film, sweat, blood, or other bodily fluids. It should be noted, however, that sample fluid can comprise other fluids, such as milk or other beverages.

Figure 1:
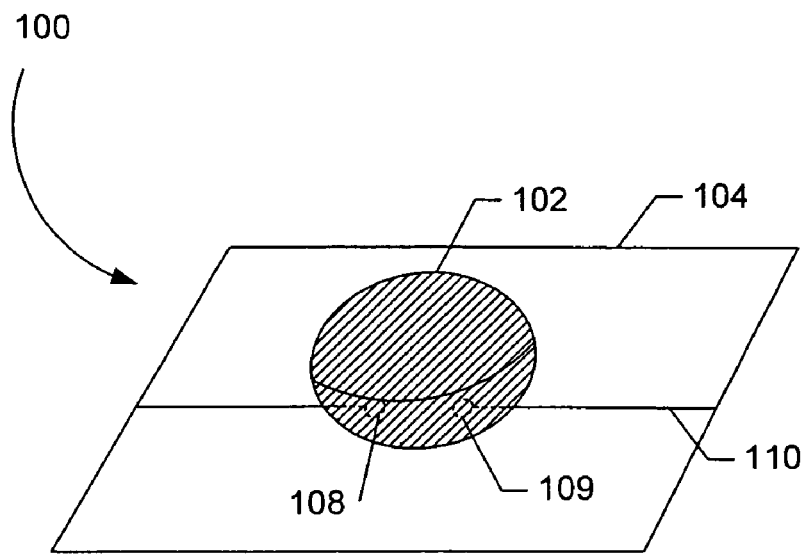
FIG. 1 illustrates an aliquot-sized sample receiving chip for measuring the osmolarity of a sample fluid.

FIG. 1 illustrates an exemplary embodiment of an osmolarity chip 100 that can be used to measure the osmolarity of a sample fluid 102, such as a tear film sample. In the FIG. 1 embodiment, the chip 100 includes a substrate 104 with a sample region having sensor electrodes 108, 109 and circuit connections 110 imprinted on the substrate. The electrodes and circuit connections are preferably printed using well-known photolithographic techniques. For example, current techniques enable the electrodes 108, 109 to have a diameter in the range of approximately one (1) to eighty (80) microns, and spaced apart sufficiently so that no conductive path exists in the absence of sample fluid. Currently available techniques, however, can provide electrodes of less than one micron in diameter, and these are sufficient for a chip constructed in accordance with the invention. The amount of sample fluid needed for measurement is no more than is necessary to extend from one electrode to the other, thereby providing an operative conductive path. The photolithographic scale of the chip 100 permits the measurement to be made for aliquot-sized samples in a micro- or nano-scale level. For example, reliable osmolarity measurement can be obtained with a sample volume of less than 20 μL of tear film. A typical sample volume is less than one hundred nanoliters (100 nL). It is expected that it will be relatively easy to collect 10 nL of a tear film sample even from patients suffering from dry eye.

The chip 100 is configured to transfer energy to the sample fluid 102 and enable detection of the sample fluid energy properties. In this regard, a current source is applied across the electrodes 108, 109 through the connections 110. The osmolarity of the sample fluid can be measured by sensing the energy transfer properties of the sample fluid 102. The energy transfer properties can include, for example, electrical conductivity, such that the impedance of the sample fluid is measured, given a particular amount of electrical power (e.g., current) that is transferred into the sample through the connections 110 and the electrodes 108, 109.

If conductivity of the sample fluid is to be measured, then preferably a sinusoidal signal on the order of ten volts at approximately 10 kHz is applied. The real and imaginary parts of the complex impedance of the circuit path from one electrode 108 through the sample fluid 102 to the other electrode 109 are measured. At the frequencies of interest, it is likely that the majority of the electrical signal will be in the real half of the complex plane, which reduces to the conductivity of the sample fluid. This electrical signal (hereafter referred to as conductivity) can be directly related to the ion concentration of the sample fluid 102, and the osmolarity can be determined. Moreover, if the ion concentration of the sample fluid 102 changes, the electrical conductivity and the osmolarity of the fluid will change in a corresponding manner. Therefore, the osmolarity is reliably obtained. In addition, because the impedance value does not depend on the volume of the sample fluid 102, the osmolarity measurement can be made substantially independent of the sample volume.

As an alternative to the input signal described above, more complex signals can be applied to the sample fluid whose response will contribute to a more thorough estimate of osmolarity. For example, calibration can be achieved by measuring impedances over a range of frequencies. These impedances can be either simultaneously (via combined waveform input and Fourier decomposition) or sequentially measured. The frequency versus impedance data will provide information about the sample and the relative performance of the sample fluid measurement circuit.

Figure 2:
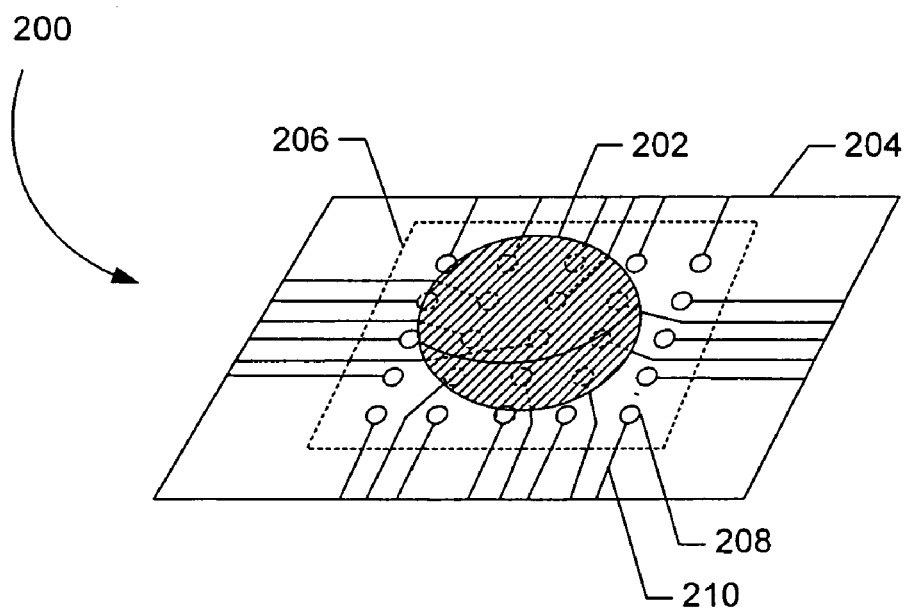
FIG. 2 illustrates an alternative embodiment of a sample receiving chip that includes a circuit region with an array of electrodes imprinted with photolithography techniques.

FIG. 2 illustrates an alternative embodiment of a sample receiving chip 200 that measures osmolarity of a sample fluid 202, wherein the chip comprises a substrate layer 204 with a sample region 206 comprising an imprinted circuit that includes an array of electrodes 208. In the illustrated embodiment of FIG. 2, the sample region 206 has a 5-by-5 array of electrodes that are imprinted with photolithographic techniques, with each electrode 208 having a connection 210 to one side of the substrate 204. Not all of the electrodes 208 in FIG. 2 are shown with a connection, for simplicity of illustration. The electrodes provide measurements to a separate processing unit, described further below.

The electrode array of FIG. 2 provides a means to measure the size of the tear droplet 202 by detecting the extent of conducting electrodes 208 to thereby determine the extent of the droplet. In particular, processing circuitry can determine the number of electrodes that are conducting, and therefore the number of adjacent electrodes that are covered by the droplet 202 will be determined. The planar area of the substrate that is covered by the sample fluid is thereby determined. With a known nominal surface tension of the sample fluid, the height of the sample fluid volume over the planar area can be reliably estimated, and therefore the volume of the droplet 202 can be determined.

Figure 3:
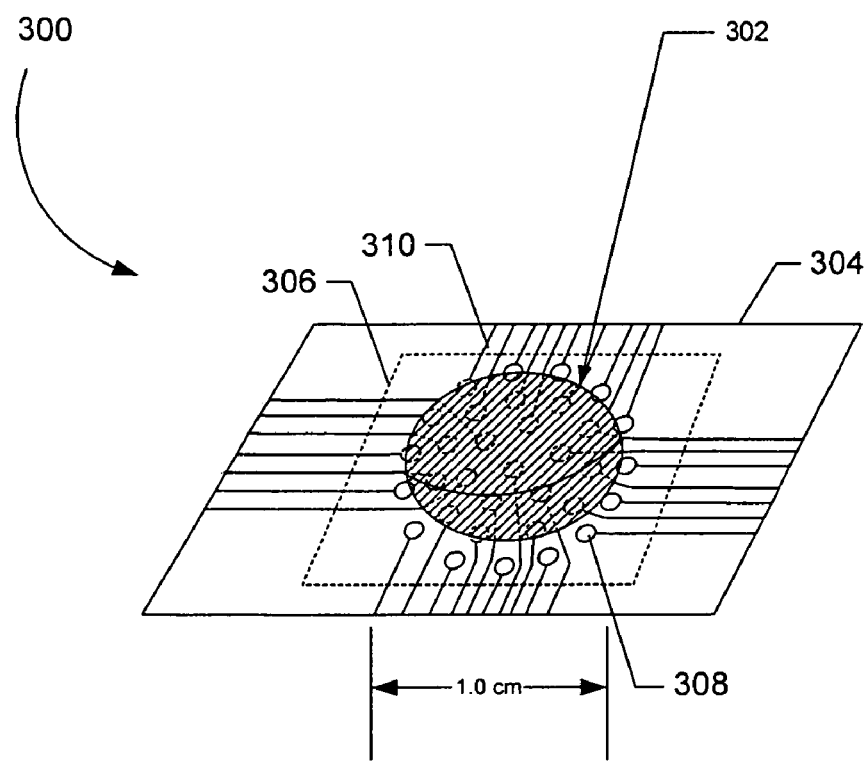
FIG. 3 illustrates another alternative embodiment of the FIG. 1 chip, wherein a circuit region includes printed electrodes arranged in a plurality of concentric circles.

FIG. 3 illustrates another alternative embodiment of a sample receiving chip 300 on which a sample fluid 302 is deposited. The chip comprises a substrate layer 304, wherein a sample region 306 is provided with electrodes 308 that are configured in a plurality of concentric circles. In a manner similar to the square array of FIG. 2, the circular arrangement of the FIG. 3 electrodes 308 also provides an estimate of the size of the sample fluid volume 302 because the droplet typically covers a circular or oval area of the sample region 302. Processing circuitry can detect the largest (outermost) circle of electrodes that are conducting, and thereby determine a planar area of coverage by the fluid sample. As before, the determined planar area provides a volume estimate, in conjunction with a known surface tension and corresponding volume height of the sample fluid 302. In the FIG. 3 illustrated embodiment, the electrodes 308 can be printed using well-known photolithography techniques that currently permit electrodes to have a diameter in the range of one (1) to eighty (80) microns. This allows the sub-microliter droplet to substantially cover the electrodes. The electrodes can be printed over an area sized to receive the sample fluid, generally covering 1 mm$^2$ to 1 cm$^2$.

The electrodes and connections shown in FIG. 1, FIG. 2, and FIG. 3 can be imprinted on the respective substrate layers as electrodes with contact pads, using photolithographic techniques. For example, the electrodes can be formed with different conductive metalization such as aluminum, platinum, titanium, titanium-tungsten, and other similar material. In one embodiment, the electrodes can be formed with a dielectric rim to protect field densities at the edges of the electrodes. This can reduce an otherwise unstable electric field at the rim of the electrode.

Figure 4:
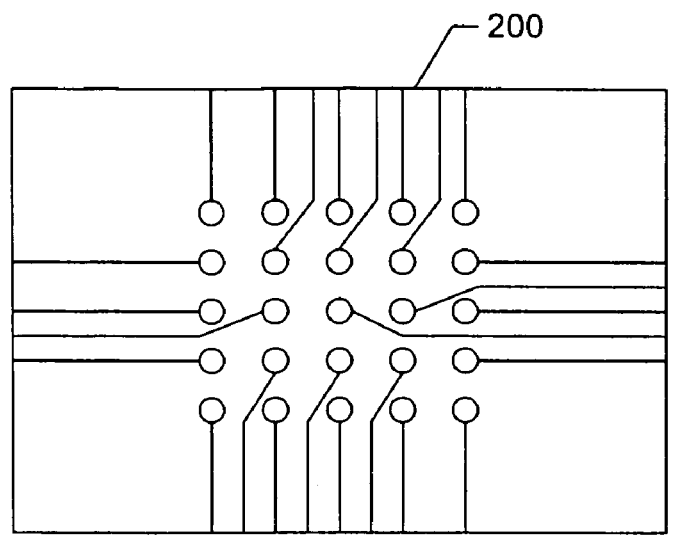
FIG. 4 is a top view of the chip shown in FIG. 2.
Figure 5:
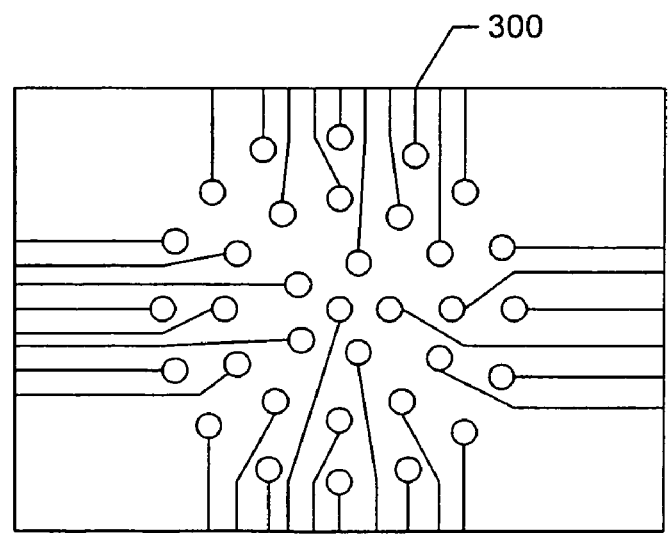
FIG. 5 is a top view of the chip shown in FIG. 3.

Top views of the exemplary embodiments of the chips 200 and 300 are illustrated in FIG. 4 and FIG. 5, respectively. The embodiments show the detailed layout of the electrodes and the connections, and illustrate how each electrode can be electrically connected for measuring the electrical properties of a sample droplet. As mentioned above, the layout of the electrodes and the connections can be imprinted on the substrate 100, 200, 300 using well-known photolithographic techniques.

Figure 6:
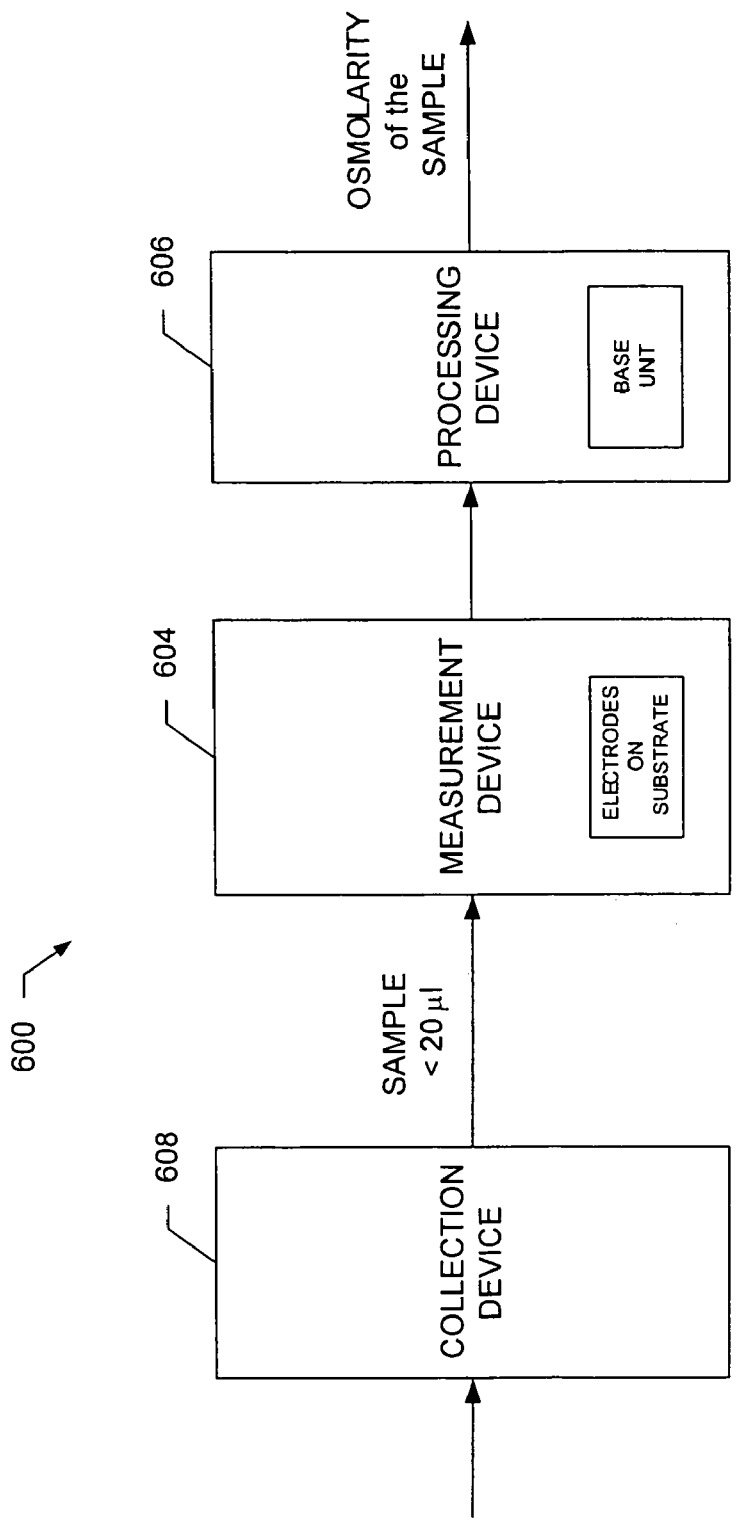
FIG. 6 is a block diagram of an osmolarity measurement system configured in accordance with the present invention.

FIG. 6 is a block diagram of an osmometry system 600 configured in accordance with an embodiment of the present invention, showing how information is determined and used in a process that determines osmolarity of a sample fluid. The osmometry system 600 includes a measurement device 604 and a processing device 606. The measurement device receives a volume of sample fluid from a collection device 608. The collection device can comprise, for example, a micropipette or capillary tube. The collection device 608 collects a sample tear film of a patient, such as by using negative pressure from a fixed-volume micropipette or charge attraction from a capillary tube to draw a small tear volume from the vicinity of the ocular surface of a patient.

The measurement device 604 can comprise a system that transfers energy to the fluid in the sample region and detects the imparted energy. For example, the measurement device 604 can comprise circuitry that provides electrical energy in a specified waveform (such as from a function generator) to the electrical path comprising two electrodes bridged by the sample fluid. The processing device 606 detects the energy imparted to the sample fluid and determines osmolarity. The processing device can comprise, for example, a system including an RLC multimeter that produces data relating to the reactance of the fluid that forms the conductive path between two electrodes, and including a processor that determines osmolarity through a table look-up scheme. If desired, the processing device can be housed in a base unit that receives one of the chips described above.

As mentioned above, a sample sufficient to provide an osmolarity measurement can contain less than 20 microliters (µL) of fluid. A typical sample of tear film in accordance with the invention is collected by a fluid collector such as a capillary tube, which often contains less than one microliter of tear film. Medical professionals will be familiar with the use of micropipettes and capillary tubes, and will be able to easily collect the small sample volumes described herein, even in the case of dry eye sufferers.

The collected sample fluid is expelled from the collection device 608 to the measurement device 604. The collection device can be positioned above the sample region of the chip substrate either manually by a medical professional or by being mechanically guided over the sample region. In one embodiment, for example, the collection device (e.g., a capillary tube) is mechanically guided into position with an injection-molded plastic hole in a base unit, or is fitted to a set of clamps with precision screws (e.g., a micromanipulator with needles for microchip interfaces). In another embodiment, the guide is a computer-guided feedback control circuitry that holds the capillary tube and automatically lowers it into the proper position.

The electrodes and connections of the chips measure energy properties of the sample fluid, such as conductivity, and enable the measured properties to be received by the processing device 606. The measured energy properties of the sample fluid include electrical conductivity and can also include other parameters, such as both parts of the complex impedance of the sample, the variance of the noise in the output signal, and the measurement drift due to resistive heating of the sample fluid. The measured energy properties are processed in the processing device 606 to provide the osmolarity of the sample. In one embodiment, the processing device 606 comprises a base unit that can accept a chip and can provide electrical connection between the chip and the processing device 606. In another embodiment, the base unit can include a display unit for displaying osmolarity values. It should be noted that the processing device 606 and, in particular, the base unit can be a hand-held unit.

Figure 7:
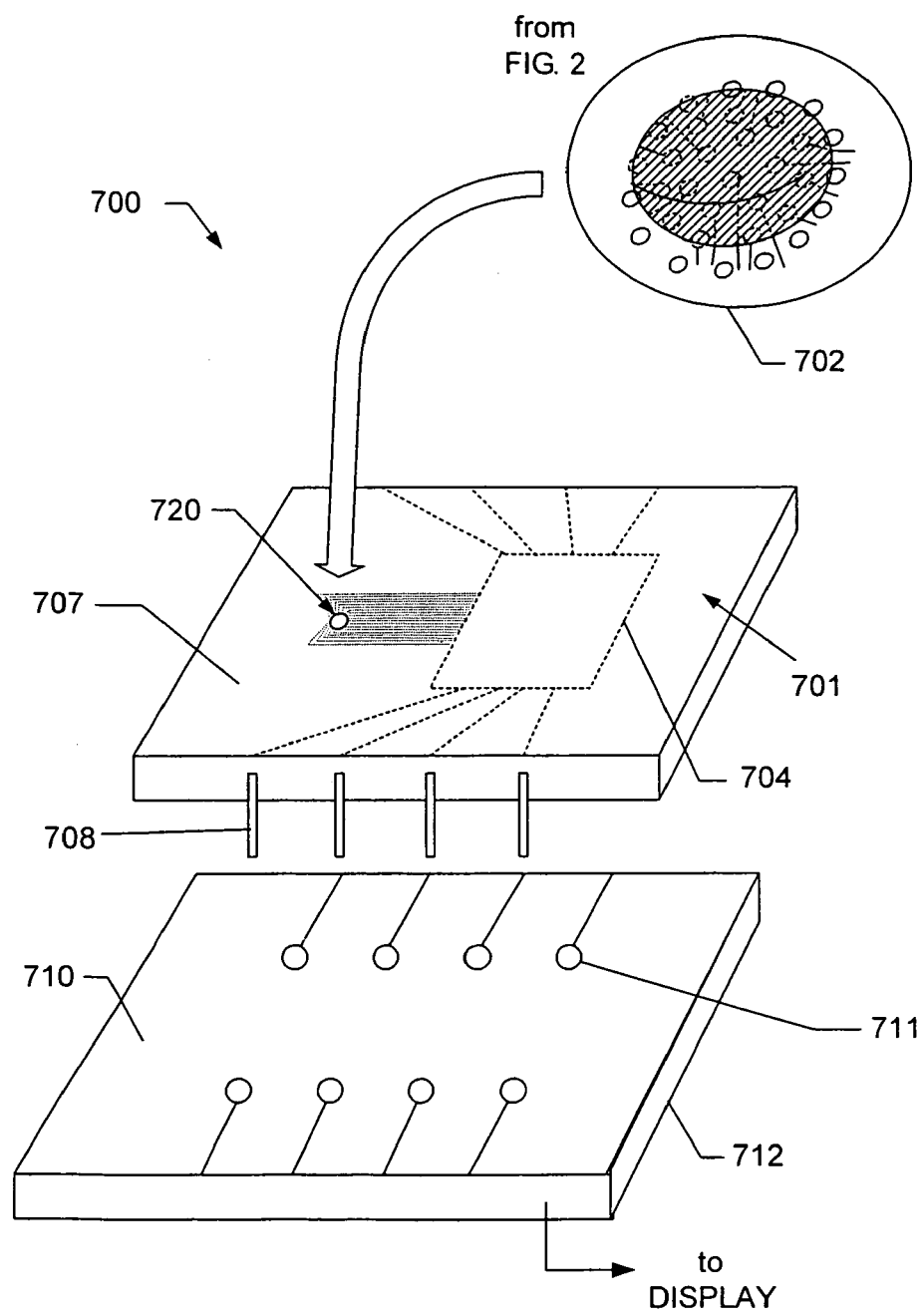
FIG. 7 is a perspective view of a tear film osmolarity measurement system constructed in accordance with the present invention.

FIG. 7 is a perspective view of a tear film osmolarity measuring system 700 constructed in accordance with the present invention. In the illustrated embodiment of FIG. 7, the exemplary system 700 includes a measuring unit 701 that comprises a chip, such as one of the chips described above, and a connector or socket base 710, which provides the appropriate measurement output. The system 700 determines osmolarity by measuring electrical conductivity of the sample fluid. Therefore, the measurement chip 701 comprises a semiconductor integrated circuit (IC) chip with a substrate having a construction similar to that of the chips described above in connection with FIG. 1 through FIG. 5. Thus, the chip 701 includes a substrate layer with a sample region that is defined by at least two electrodes printed onto the substrate layer (such details are of a scale too small to be visible in FIG. 7; see FIG. 1 through FIG. 5). The substrate and sample region are encased within an inert package, in a manner that will be known to those skilled in the art. In particular, the chip 701 is fabricated using conventional semiconductor fabrication techniques into an IC package 707 that includes electrical connection legs 708 that permit electrical signals to be received by the chip 701 and output to be communicated outside of the chip. The packaging 707 provides a casing that makes handling of the chip more convenient and helps reduce evaporation of the sample fluid.

Figure 8:
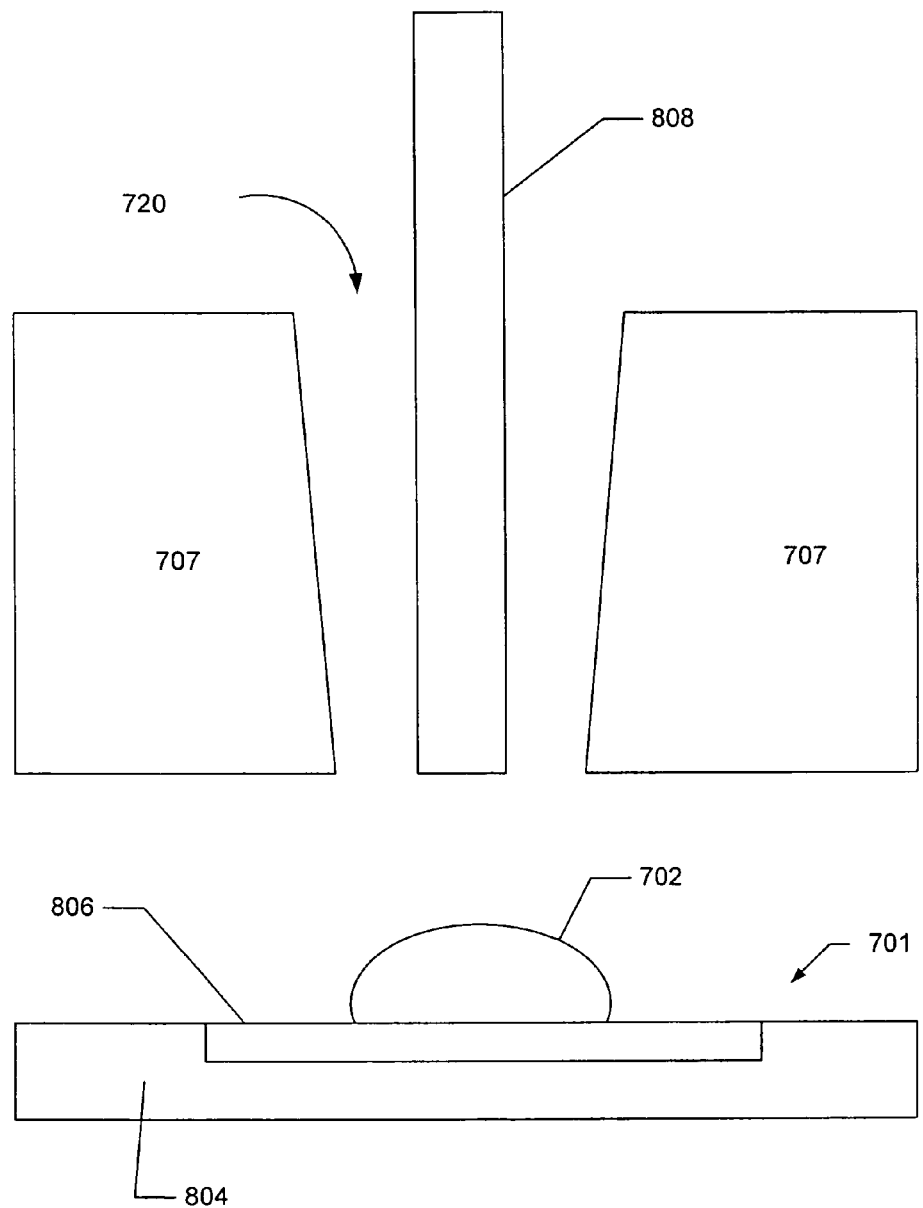
FIG. 8 is a side section of the sample receiving chip showing the opening in the exterior packaging.

FIG. 8 shows that the measurement chip 701 is fabricated with an exterior opening hole 720 into which the sample fluid 702 is inserted. Thus, the hole 720 can be formed in the semiconductor packaging 707 to provide a path through the chip exterior to the substrate 804 and the sample region 806. The collection device (such as a micropipette or capillary tube) 808 is positioned into the hole 720 such that the sample fluid 702 is expelled from the collection device directly onto the sample region 806 of the substrate 804. The hole 720 is sized to receive the tip of the collection device. The hole 720 forms an opening or funnel that leads from the exterior of the chip onto the sample region 806 of the substrate 804. In this way, the sample fluid 702 is expelled from the collection device 808 and is deposited directly on the sample region 806 of the substrate 804. The sample region is sized to receive the volume of sample fluid from the collection device. In FIG. 8, for example, the electrodes form a sample region 806 that is generally in a range of approximately 1 $mm^2$ to 1 $cm^2$ in area.

Returning to FIG. 7, the chip 701 can include processing circuitry 704 that comprises, for example, a function generator that generates a signal of a desired waveform, which is applied to the sample region electrodes of the chip, and a voltage measuring device to measure the root-mean-square (RMS) voltage value that is read from the chip electrodes. The function generator can produce high frequency alternating current (AC) to avoid undesirable direct current (DC) effects for the measurement process. The voltage measuring device can incorporate the functionality of an RLC measuring device. Thus, the chip 701 can incorporate the measurement circuitry as well as the sample region electrodes. The processing circuitry can include a central processing unit (CPU) and associated memory that can store programming instructions (such as firmware) and also can store data. In this way, a single chip can include the electrodes and associated connections for the sample region, and on a separate region of the chip, can also include the measurement circuitry. This configuration will minimize the associated stray resistances of the circuit structures.

As noted above, the processing circuitry 704 applies a signal waveform to the sample region electrodes. The processing circuitry also receives the energy property signals from the electrodes and determines the osmolarity value of the sample fluid. For example, the processing unit receives electrical conductivity values from a set of electrode pairs. Those skilled in the art will be familiar with techniques and circuitry for determining the conductivity of a sample fluid that forms a conducting path between two or more electrodes.

Figure 9:
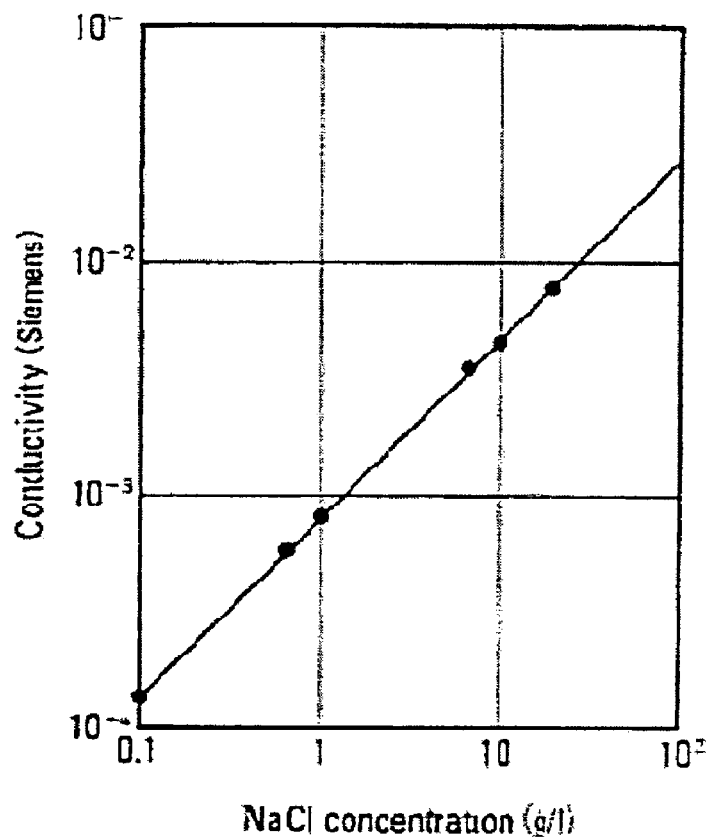
FIG. 9 is a calibration curve relating the sodium content of the sample fluid with electrical conductivity.

In the FIG. 7 embodiment, the processing unit 704 produces signal waveforms at a single frequency, such as 100 kHz and 10 Volts peak-to-peak. The processing circuitry 704 then determines the osmolarity value from the sodium content correlated to the electrical conductivity using a calibration curve, such as the curve shown in FIG. 9. In this case, the calibration curve is constructed as a transfer function between the electrical conductivity (voltage) and the osmolarity value (i.e., the sodium content). It should be noted, however, that other calibration curves can also be constructed to provide transfer functions between other energy properties and the osmolarity value. For example, the variance, autocorrelation and drift of the signal can be included in an osmolarity calculation. If desired, the osmolarity value can also be built upon multi-variable correlation coefficient charts or neural network interpretation so that the osmolarity value can be optimized with an arbitrarily large set of measured variables.

In an alternate form of the FIG. 7 embodiment, the processing unit 704 produces signal waveforms of a predetermined frequency sweep, such as 1 kHz to 100 kHz in 1 kHz increments, and stores the conductivity and variance values received from the set of electrode pairs at each frequency. The output signal versus frequency curve can then be used to provide higher order information about the sample which can be used with the aforementioned transfer functions to produce an ideal osmolarity reading.

As shown in FIG. 7, the base socket connector 710 receives the pins 708 of the chip 701 into corresponding sockets 711.

The connector 710, for example, can supply the requisite electrical power to the processing circuitry 704 and electrodes of the chip. Thus, the chip 701 can include the sample region electrodes and the signal generator and processing circuitry necessary for determining osmolarity, and the output comprising the osmolarity value can be communicated off the chip via the pins 708 through the connector 710 and to a display readout.

If desired, the base connector socket 710 can include a Peltier layer 712 located beneath the sockets that receive the pins 708 of the chip 701. Those skilled in the art will understand that a Peltier layer comprises an electrical/ceramic junction such that properly applied current can cool or heat the Peltier layer. In this way, the sample chip 701 can be heated or cooled, thereby further controlling evaporation of the sample fluid. It should be apparent that evaporation of the sample fluid should be carefully controlled, to ensure accurate osmolarity values obtained from the sample fluid.

Figure 10:
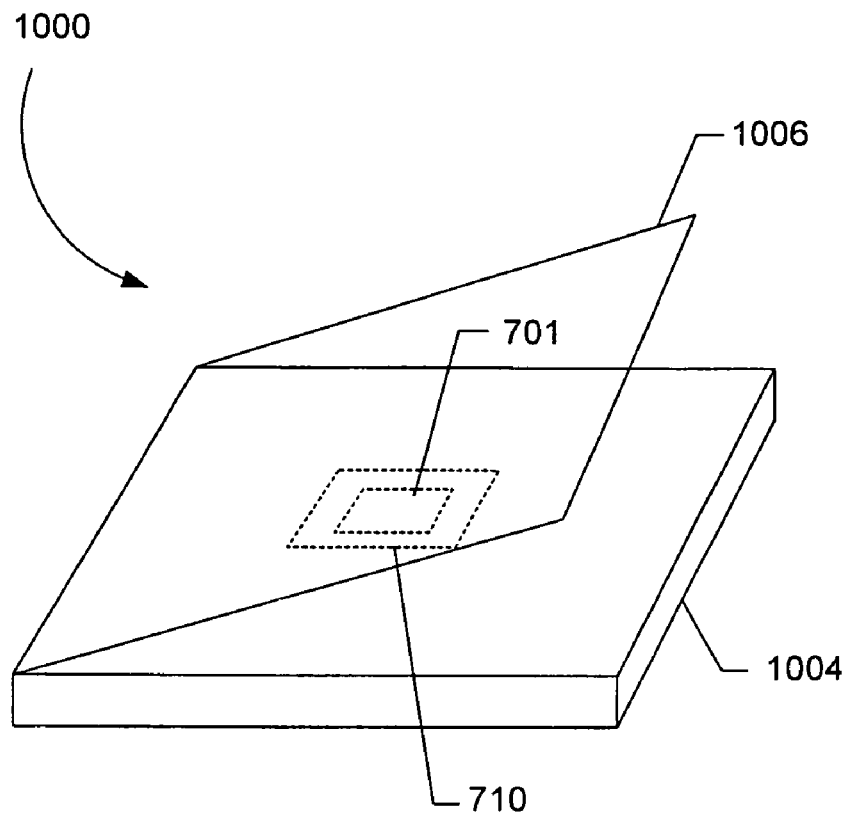
FIG. 10 illustrates a hinged base unit of the osmometer that utilizes the sample receiving chips described in FIGS. 1-5.

FIG. 10 shows an alternative embodiment of an osmometer in which the chip does not include an on-chip processing unit such as described above, but rather includes limited circuitry comprising primarily the sample region electrodes and interconnections. That is, the processing unit is separately located from the chip and can be provided in the base unit.

FIG. 10 shows in detail an osmometer 1000 that includes a base unit 1004, which houses the base connector 710, and a hinged cover 1006 that closes over the base connector 710 and a received measurement chip 701. Thus, after the sample fluid has been dispensed on the chip, the chip is inserted into the socket connector 710 of the base unit 1004 and the hinged cover 1006 is closed over the chip to reduce the rate of evaporation of the sample fluid.

It should be noted that the problem with relatively fast evaporation of the sample fluid can generally be handled in one of two ways. One way is to measure the sample fluid voltage quickly as soon possible after the droplet is placed on the sample region of the chip. Another way is to enable the measuring unit to measure the rate of evaporation along with the corresponding changes in conductivity values. The processing unit can then post-process the output to estimate the osmolarity value. The processing can be performed in the hardware or in software stored in the hardware. Thus, the processing unit can incorporate different processing techniques such as using neural networks to collect and learn about characteristics of the fluid samples being measured for osmolarity, as well as temperature variations, volume changes, and other related parameters so that the system can be trained in accordance with neural network techniques to make faster and more accurate osmolarity measurements.

Figure 11:
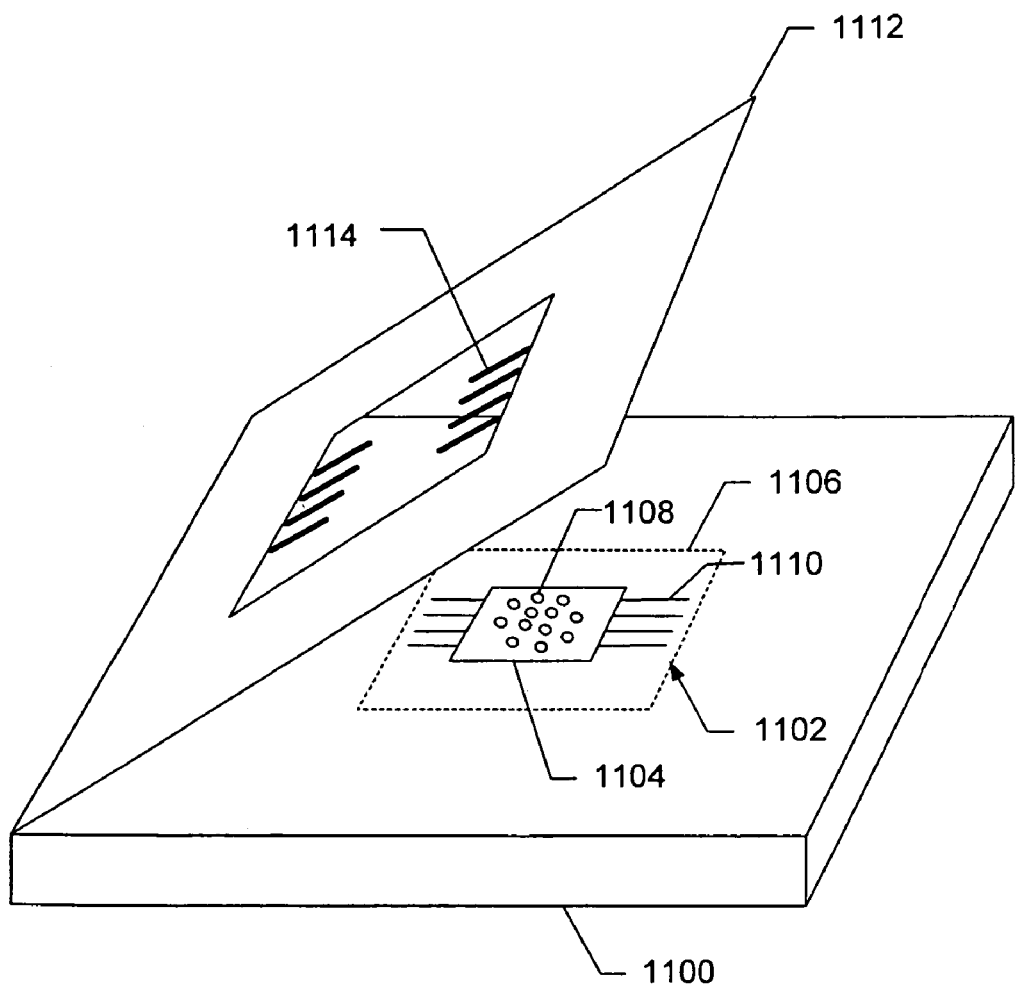
FIG. 11 illustrates a probe card configuration for the sample receiving chip and processing unit.

FIG. 11 shows another alternative construction, in which the osmolarity system utilizes a sample receiving chip 1102 that does not include IC packaging such as shown in FIG. 7. Rather, the FIG. 11 measurement chip 1102 is configured as a chip with an exposed sample region comprising the electrodes and associated connections, but the processing circuitry is located in the base unit for measuring the energy properties of the sample fluid. In this alternative construction, a connector similar to the connector socket 710 allows transmission of measured energy properties to the processing unit in the base unit. Those skilled in the art will understand that such a configuration is commonly referred to a probe card structure.

FIG. 11 shows a probe card base unit 1100 that receives a sample chip probe card 1102 that comprises a substrate 1104 with a sample region 1106 on which are formed electrodes 1108 that are wire bonded to edge connectors 1110 of the probe card. When the hinged lid 1112 of the base unit is closed down over the probe card, connecting tines 1114 on the underside of the lid come into mating contact with the edge connectors 1110. In this way, the electrodes of the sample region 1106 are coupled to the processing circuitry and measurement can take place. The processing circuitry of the probe card embodiment of FIG. 11 can be configured in either of the configurations described above. That is, the processing to apply current to the electrodes and to detect energy properties of the sample fluid and determine osmolarity can be located on-chip, on the substrate of the probe card 1102, or the processing circuitry can be located off-chip, in the base unit 1100.

In all the alternative embodiments described above, the osmometer is used by placing a new measurement chip into the base unit while the hinged top is open. Upon placement into the base unit, the chip is powered up and begins monitoring its environment. Recording output signals from the chip at a rate of, for example, 1 kHz, will fully capture the behavior of the system. Placing a sample onto any portion of the electrode array generates high signal-to-noise increase in conductivity between any pair of electrodes covered by the sample fluid. The processing unit will recognize the change in conductivity as being directly related to the addition of sample fluid, and will begin conversion of electronic signals into osmolarity data once this type of change is identified. This strategy occurs without intervention by medical professionals. That is, the chip processing is initiated upon coupling to the base unit and is not dependent on operating the lid of the base unit or any other user intervention.

In any of the configurations described above, either the "smart chip" with processing circuitry on-chip (FIG. 7), or the electrode-only configuration with processing circuitry off-chip (FIG. 10), in a packaged chip (FIG. 7 and FIG. 10) or in a probe card (FIG. 11), the sample receiving chip can be disposed of after each use, so that the base unit serves as a platform for interfacing with the disposable measurement chip. As noted, the base unit can also include relevant control, communication, and display circuits (not shown), as well as software, or such features can be provided off-chip in the base unit. In this regard, the processing circuitry can be configured to automatically provide sufficient power to the sample region electrodes to irreversibly oxidize them after a measurement cycle, such that the electrodes are rendered inoperable for any subsequent measurement cycle. Upon inserted a used chip into the base unit, the user will be given an indication that the electrodes are inoperable. This helps prevent inadvertent multiple use of a sample chip, which can lead to inaccurate osmolarity readings and potentially unsanitary conditions.

A secondary approach to ensure that a previously used chip is not placed back into the machine includes encoding serial numbers, or codes directly onto the chip. The base unit will store the used chip numbers in memory and cross-reference them against new chips placed in the base connector. If the base unit finds that the serial number of the used chip is the same as an old chip, then the system will refuse to measure osmolarity until a new chip is inserted. It is important to ensure use of a new chip for each test because proteins adsorb and salt crystals form on the electrodes after evaporation has run its course, which corrupt the integrity of the measuring electrodes.

Figure 12:
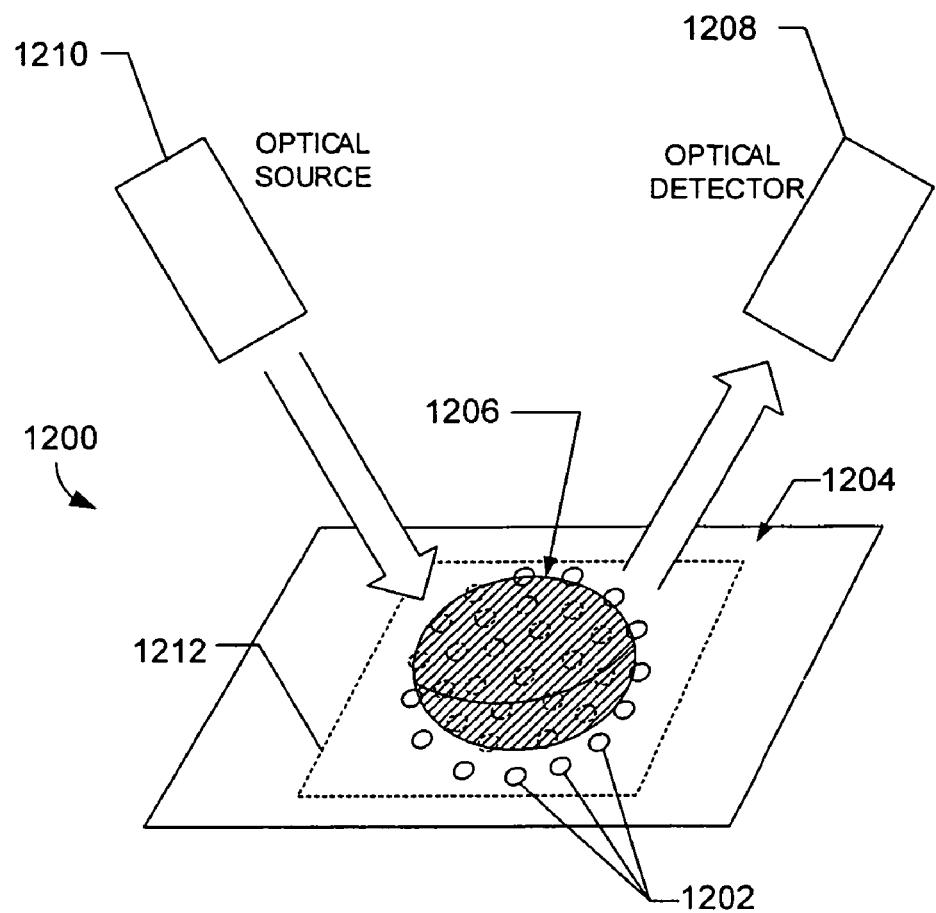
FIG. 12 illustrates an optical osmolarity measurement system constructed in accordance with the present invention.

In a further embodiment shown. in FIG. 12, the osmolarity of a sample fluid can be measured optically in an optical measurement system 1200 by using optical indicators 1202 disposed on a measuring region 1212 of the chip substrate 1204. The optical indicators 1202 can comprise, for example, nano-scale spheres, also called nanobeads, that are coated with chemicals whose fluorescence varies with exposure to sample fluid of varying osmolarity, i.e. ionophores. The nanobeads 1202 can be deposited on the chip substrate 1204 on top of the electrodes described above for the conductivity-measuring chips. The electrodes are useful for determining the volume of the sample fluid, as described above. However, other volume-measuring elements may be used to determine the volume of the sample fluid. Preferably, the optical chip is produced with inert packaging such as described above in connection with FIG. 7, including a chip opening hole through which the collection device tip can be inserted. The sample fluid is then expelled from the collection device and the sample fluid comes into contact with a predetermined, fixed number of the nano beads per electrode site, which become immersed in the sample fluid.

When the nanobeads 1202 are illuminated with an optical energy source 1210, such as a laser, the beads 1202 will fluoresce in accordance with the osmolarity of the sample fluid 1206. The fluorescence can be detected using a suitable optical detector light receiving device 1208, such as a conventional charge-coupled device (CCD) array, photodiode, or the like. The resulting output signal of the light receiving array can indicate the osmolarity value of the sample fluid. It should be noted that the nano-scale beads are sized such that an aliquot-sized fluid sample 1206 (i.e., no more than 20 microliters of the fluid) will ordinarily produce sufficient fluorescence to provide an output signal, that can be detected by the light receiving device 1208 and that can indicate osmolarity of the sample fluid. The amount of fluorescence can be normalized by calculating how many nanobeads were activated by fluid, by measuring which electrode pairs were activated by the sample fluid. This normalization accounts for the sample volume and allows the volume independence feature of the prior embodiment to be retained.

Figure 13:
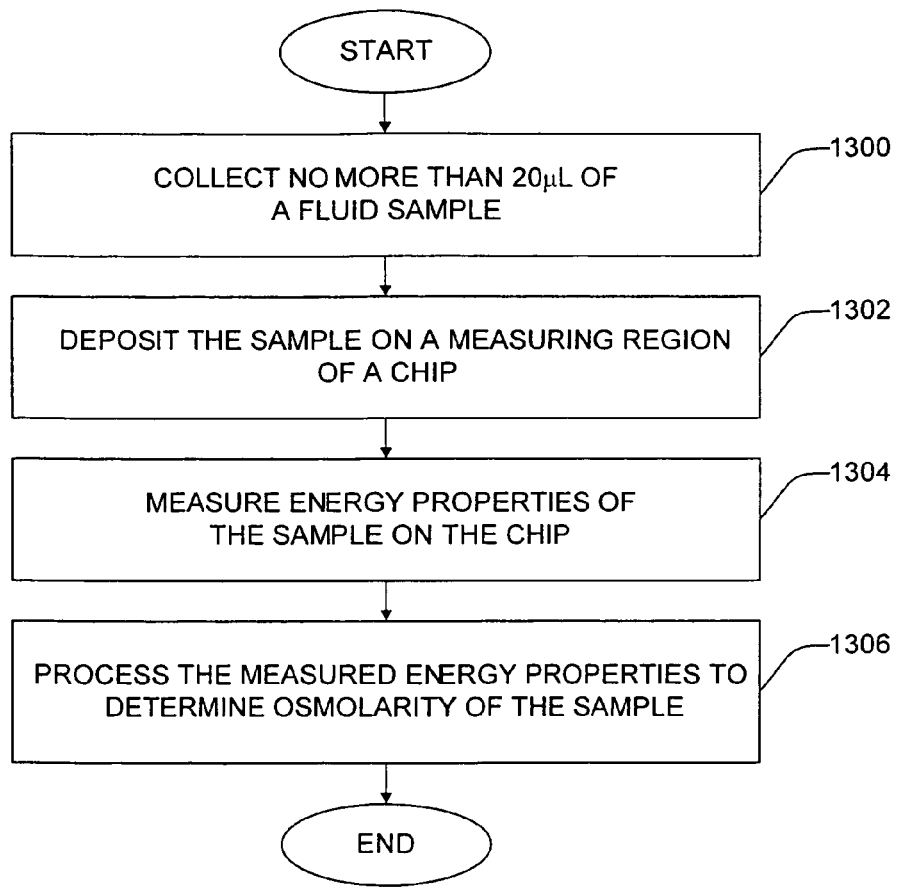
FIG. 13 is a flowchart describing an exemplary osmolarity measurement technique in accordance with the invention.

FIG. 13 is a flowchart describing an exemplary osmolarity measurement technique in accordance with the invention. A body fluid sample, such as a tear film, is collected at box 1300. The sample typically contains less than one microliter. At box 1302, the collected sample is deposited on a sample region of the chip substrate. The energy properties of the sample are then measured at box 1304. The measured energy properties are then processed, at box 1306, to determine the osmolarity of the sample. If the chip operates in accordance with electrical conductivity measurement, then the measurement processing at box 1306 can include the "electrode oxidation" operation described above that renders the chip electrodes inoperable for any subsequent measuring cycles.

In the measurement process for a conductivity measuring system, a substantially instantaneous shift is observed from the open circuit voltage to a value that closely represents the state of the sample at the time of collection, upon placement of a sample tear film on an electrode array of the substrate. Subsequently, a drift in the conductivity of the sample will be reflected as a continual change in the output.

The output of the measurement chip can be a time-varying voltage that is translated into an osmolarity value. Thus, in a conductivity-based system, more information than just the "electrical conductivity" of the sample can be obtained by measuring the frequency response over a wide range of input signals, which improves the end stage processing. For example, the calibration can be made over a multiple frequencies (e.g., measure ratio of signals at 10, 20, 30, 40, 50, 100 Hz) to make the measurement process a relative calculation. This makes the chip-to-chip voltage drift small. The standard method for macroscale electrode based measurements (i.e. in a pH meter, or microcapillary technique) is to rely upon known buffers to set up a linear calibration curve. Because photolithography is an extremely reproducible manufacturing technique, when coupled to a frequency sweep, calibration can be performed without operator intervention.

As mentioned above, the processing of the energy properties can be performed in a neural network configuration, where the seemingly disparate measured data points obtained from the energy properties can be used to provide more accurate osmolarity reading than from a single energy property measurement. For example, if only the electrical conductivity of the sample is measured, then the calibration curve can be used to simply obtain the osmolarity value corresponding to the conductivity. This osmolarity value, however, generally will not be as accurate as the output of the neural network.

The neural network can be designed to operate on a collection of calibration curves that reflects a substantially optimized transfer function between the energy properties of the sample fluid and the osmolarity. Thus, in one embodiment, the neural network constructs a collection of calibration curves for all variables of interest, such as voltage, evaporation rate and volume change. The neural network can also construct or receive as an input a priority list that assigns an importance factor to each variable to indicate the importance of the variable to the final outcome, or the osmolarity value. The neural network constructs the calibration curves by training on examples of real data where the final outcome is known a priori. Accordingly, the neural network will be trained to predict the final outcome from the best possible combination of variables. This neural network configuration that processes the variables in an efficient combination is then loaded into the processing unit residing in the measurement chip 701 or the base unit. Once trained, the neural network can be configured in software or hardware.

Although the embodiments described above for measuring osmolarity provides substantial advantage over the conventional osmolarity measuring techniques such as a freezing point depression technique, the teachings of the present invention can be used to determine osmolarity of a sample in accordance with the freezing point depression technique. Accordingly, the exemplary osmometry system 600 of FIG. 6 can be used to provide an osmolarity value based on the freezing point depression technique.

The freezing point depression system involves collecting and depositing the sample fluid in a similar manner as in the boxes 1300 and 1302 of the flowchart in FIG. 13. As noted above, however, the osmometer of the osmometer system can include a cooling device, such as a Peltier cooling device. In the FIG. 7 embodiment described above, the Peltier device is disposed on the socket 710 or the chip 701 (see FIG. 7) to cool the sample. If desired, the Peltier cooling device can be used to cool the sample fluid to the freezing point of the sample fluid. A photo-lithographed metal junction, or p-n junction, known as a thermocouple, can be used to monitor the temperature of aliquot-sized samples. The thermocouple would operate in parallel to the electrode array and Peltier cooling device, where the chip would be cooled below freezing so that the sample becomes a solid. Upon solidification, the electrical conductivity of the sample will drastically change. Because the thermocouple is continually measuring the temperature, the point at which the conductivity spikes can be correlated to the depressed freezing point. Alternatively, the chip could be supercooled immediately prior to sample introduction by the Peltier unit, and then by using the resistive heating inherent to the electrodes, a current can be passed along the solid phase material. Upon melting, the conductivity will again drastically change. In the second measurement technique, it is likely that evaporation will be less of a factor. Thus, the present invention permits freezing point depression to be performed at significantly smaller volumes of sample fluid than previously possible.

The present invention has been described above in terms of exemplary embodiments so that an understanding of the present invention can be conveyed. Any embodiment described herein as "exemplary" is not necessarily to be construed as preferred or advantageous over other embodiments. Moreover, there are many configurations for the osmometer and associated components not specifically described herein but with which the present invention is applicable. The present invention should therefore not be seen as limited to the particular embodiments described herein, but rather, it should be understood that the present invention has wide applicability with respect to tear film osmometry generally. All modifications, variations, or equivalent arrangements and implementations that are within the scope of the attached claims should therefore be considered within the scope of the invention.

I claim:

1. A sample receiving chip comprising:
   a substrate that receives an aliquot volume of a sample fluid;
   a sample region of the substrate, sized such that the volume of the sample fluid is sufficient to operatively cover a portion of the sample region, whereupon energy transfer properties of the sample fluid can be detected from the sample region to produce a sample fluid reading, wherein the sample fluid reading is related to the sample fluid energy transfer properties and indicates osmolarity of the sample fluid;
   wherein the sample fluid includes a bodily fluid.

2. A chip as defined in claim 1, wherein the sample region includes a plurality of electrodes disposed to contact the sample.

3. A chip as defined in claim 2, wherein the plurality of electrodes is arranged in a row and column array.

4. A chip as defined in claim 2, further comprising a plurality of conductive connection lines coupled to the plurality of electrodes, wherein the conductive connection lines provide means for transferring energy to and from the sample fluid.

5. A chip as defined in claim 4, further comprising:
   a processing unit configured to receive energy properties of the sample fluid from the plurality of conductive connection lines, wherein the processing unit processes the received energy properties and outputs the osmolarity of the sample fluid.

6. A chip as defined in claim 1, wherein area of the sample region on the substrate is less than about one centimeter square.

7. A chip as defined in claim 1, further comprising:
   a temperature control element in communication with the substrate.

8. A chip as defined in claim 7, wherein the temperature control element includes a Peltier cooling device.

9. A chip as defined in claim 1, wherein the bodily fluid is a tear film.

10. A sample receiving chip comprising:
    a substrate that receives an aliquot volume of a sample fluid;
    a sample region of the substrate, sized such that the volume of the sample fluid is sufficient to operatively cover a portion of the sample region, whereupon energy transfer properties of the sample fluid can be detected from the sample region to produce a sample fluid reading, wherein the sample fluid reading is related to the sample fluid energy transfer properties and indicates osmolarity of the sample fluid;
    wherein the sample fluid includes beverages.

11. An osmolarity measuring system for measuring osmolarity of a sample fluid, the system comprising:
    a measurement device comprising a sample receiving chip that includes a substrate having a sample region configured to contact the sample fluid to produce a sample fluid reading that is related to energy transfer properties of the sample fluid, wherein the region is sized to be substantially covered by an aliquot volume of the sample fluid; and
    a processing device coupled to the measurement device, the processing device configured to receive the sample fluid reading and to process and estimate the osmolarity of the sample fluid from the processed energy transfer properties;
    wherein the measurement device includes a plurality of electrodes.

12. A system as defined in claim 11, wherein the substrate includes an electrical conductivity measurement circuit.

13. A system as defined in claim 11, wherein the electrodes are formed with aluminum material.

14. A system as defined in claim 11, wherein the electrodes are formed with platinum material.

15. A system as defined in claim 11, wherein the electrodes are formed with titanium material.

16. A system as defined in claim 11, wherein the electrodes are formed with titanium-tungsten material.

17. A method for determining osmolarity value of sample fluid comprising:
    depositing an aliquot volume of the sample fluid on a sample region of a substrate;
    measuring energy transfer properties of the sample fluid; and
    processing the measured energy transfer properties to provide the osmolarity value of the sample fluid;
    further comprising collecting an appropriate amount of the sample fluid.

18. A method as defined in claim 17, wherein measuring energy transfer properties includes measuring the electrical conductivity of the sample fluid.

19. A method as defined in claim 17, wherein the appropriate amount of the sample fluid is no more than 20 microliters.

20. A method as defined in claim 17, wherein measuring energy transfer properties includes:
    providing a plurality of electrodes on the region of the substrate; and
    bringing the sample fluid in contact with the plurality of electrodes.

21. A method as defined in claim 17, further comprising:
    applying current to the sample fluid through the plurality of electrodes.

22. A method as in claim 17, wherein the appropriate amount of the sample fluid is less than 100 nL.

23. A sample receiving chip comprising:
    a substrate that receives an aliquot volume of a sample fluid comprising a body fluid;
    a sample region of the substrate, sized such that the volume of the sample fluid is received from the body and deposited substantially on the sample region, and is sufficient to operatively cover a portion of the sample region, wherein energy imparted into the sample fluid is transduced by the sample region ex vivo to produce an output signal that indicates energy transfer properties of the sample fluid that are correlated with osmolarity of the sample fluid;

wherein the imparted energy comprises electrical energy; and wherein the sample region comprises a plurality of electrodes such that the received sample fluid covers one or more of the electrodes and renders the electrodes conductive, and wherein the sample region further transduces the imparted electrical energy ex vivo such that the output signal indicates electrical energy transfer properties of the sample fluid that are correlated with the osmolarity of the sample fluid.

24. A sample receiving chip as defined in claim 23, wherein the electrodes are distributed across the sample region in an area of predetermined size, such that the number of conducting electrodes determines the approximate volume of the sample fluid deposited on the substrate.

25. A chip according to claims 1 to 23, wherein the bodily fluid is sweat or blood.

26. An osmolarity measuring system for measuring osmolarity of a sample fluid comprising a body fluid, the system comprising:

a measurement device comprising a sample receiving chip that includes a substrate having a sample region sized such that a received aliquot-sized volume of the sample fluid is received from the body and deposited substantially on the sample region, and is sufficient to operatively cover a portion of the sample region, wherein energy imparted into the sample fluid is transduced ex vivo by the sample region to produce an output signal that indicates energy transfer properties of the sample fluid;

a processing device that produces an osmolarity estimate of the sample fluid in accordance with the output signal;

wherein the imparted energy comprises electrical energy; and wherein the sample region comprises a plurality of electrodes such that the received sample fluid covers one or more of the electrodes and renders the electrodes conductive, and wherein the sample region further transduces ex vivo the imparted electrical energy such that the output signal indicates electrical energy transfer properties of the sample fluid that are correlated with the osmolarity of the sample fluid.

27. An osmolarity measuring system as defined in claim 26, wherein the electrodes are distributed across the sample region in an area of predetermined size, such that the number of conducting electrodes determines the approximate volume of the sample fluid deposited on the substrate.

28. A system according to claims 11 or 26, wherein the sample fluid is tear film, sweat, or blood.

29. A system according to claims 11 or 26, wherein each electrode has a dielectric perimeter to proctect field densities at the edge of the electrode.

30. A sample receiving chip comprising:

a substrate that receives an aliquot volume of a sample fluid comprising a body fluid;

a sample region of the substrate, sized such that the volume of the sample fluid is received from the body and deposited substantially on the sample region, and is sufficient to operatively cover a portion of the sample region, wherein energy imparted into the sample fluid is transduced by the sample region ex vivo to produce an output signal that indicates energy transfer properties of the sample fluid that are correlated with osmolarity of the sample fluid;

wherein the body fluid comprises tear film.

31. A sample receiving chip comprising:

a substrate that receives an aliquot volume of a sample fluid comprising a body fluid;

a sample region of the substrate, sized such that the volume of the sample fluid is received from the body and deposited substantially on the sample region, and is sufficient to operatively cover a portion of the sample region, wherein energy imparted into the sample fluid is transduced by the sample region ex vivo to produce an output signal that indicates energy transfer properties of the sample fluid that are correlated with osmolarity of the sample fluid;

wherein body fluid comprises sweat.

32. A sample receiving chip comprising:

a substrate that receives an aliquot volume of a sample fluid comprising a body fluid;

a sample region of the substrate, sized such that the volume of the sample fluid is received from the body and deposited substantially on the sample region, and is sufficient to operatively cover a portion of the sample region, wherein energy imparted into the sample fluid is transduced by the sample region ex vivo to produce an output signal that indicates energy transfer properties of the sample fluid that are correlated with osmolarity of the sample fluid;

wherein the body fluid comprises blood.

33. A chip as in any one of claims 30, 31, and 32, wherein the sample region includes a plurality of electrodes disposed to contact the sample.

34. A chip as in any one of claims 1, 10, 23, 30, 31, and 32, wherein the aliquot volume of the sample fluid is no more than 20 microliters.

35. A chip as in any one of claims 1, 10, 23, 30, 31, and 32, wherein the aliquot volume of the sample fluid is less than 100 nL.

36. An osmolarity measuring system for measuring osmolarity of a sample fluid comprising a body fluid, the system comprising:

a measurement device comprising a sample receiving chip that includes a substrate having a sample region sized such that a received aliquot-sized volume of the sample fluid is received from the body and deposited substantially on the sample region, and is sufficient to operatively cover a portion of the sample region, wherein energy imparted into the sample fluid is transduced ex vivo by the sample region to produce an output signal that indicates energy transfer properties of the sample fluid;

a processing device that produces an osmolarity estimate of the sample fluid in accordance with the output signal;

wherein the body fluid comprises tear film.

37. An osmolarity measuring system for measuring osmolarity of a sample fluid comprising a body fluid, the system comprising:

a measurement device comprising a sample receiving chip that includes a substrate having a sample region sized such that a received aliquot-sized volume of the sample fluid is received from the body and deposited substantially on the sample region, and is sufficient to operatively cover a portion of the sample region, wherein energy imparted into the sample fluid is transduced ex vivo by the sample region to produce an output signal that indicates energy transfer properties of the sample fluid;

a processing device that produces an osmolarity estimate of the sample fluid in accordance with the output signal;

wherein the body fluid comprises sweat.

38. An osmolarity measuring system for measuring osmolarity of a sample fluid comprising a body fluid, the system comprising:

a measurement device comprising a sample receiving chip that includes a substrate having a sample region sized such that a received aliquot-sized volume of the sample fluid is received from the body and deposited substantially on the sample region, and is sufficient to operatively cover a portion of the sample region, wherein energy imparted into the sample fluid is transduced ex vivo by the sample region to produce an output signal that indicates energy transfer properties of the sample fluid;

a processing device that produces an osmolarity estimate of the sample fluid in accordance with the output signal;

wherein the body fluid.

39. A system as in any one of claims 11, 26, 36, 37, and 38, wherein said sample fluid reading is electrical conductivity or impedance of the sample fluid.

* * * * *

UNITED STATES PATENT AND TRADEMARK OFFICE
CERTIFICATE OF CORRECTION

PATENT NO. : 7,574,902 B2 Page 1 of 1
APPLICATION NO. : 11/358986
DATED : August 18, 2009
INVENTOR(S) : Benjamin D. Sullivan It is certified that error appears in the above-identified patent and that said Letters Patent is hereby corrected as shown below:

Column 18, line 6
    Should read "wherein the body fluid comprises blood."

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,574,902 B2  Page 1 of 1
APPLICATION NO. : 11/358986
DATED : August 18, 2009
INVENTOR(S) : Benjamin D. Sullivan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this

Fourteenth Day of December, 2010

David J. Kappos
*Director of the United States Patent and Trademark Office*